(12) United States Patent
Sakamoto et al.

(10) Patent No.: US 11,305,129 B2
(45) Date of Patent: Apr. 19, 2022

(54) DEFIBRILLATION SYSTEM AND DEFIBRILLATION CATHETER

(71) Applicant: KANEKA CORPORATION, Osaka (JP)

(72) Inventors: Shinichiro Sakamoto, Settsu (JP); Daichi Kamiyama, Settsu (JP); Naotake Maekubo, Okaya (JP)

(73) Assignee: KANEKA CORPORATION, Osaka (JP)

( * ) Notice: Subject to any disclaimer, the term of this patent is extended or adjusted under 35 U.S.C. 154(b) by 0 days.

(21) Appl. No.: 16/965,334

(22) PCT Filed: Jan. 29, 2019

(86) PCT No.: PCT/JP2019/002880
§ 371 (c)(1),
(2) Date: Jul. 28, 2020

(87) PCT Pub. No.: WO2019/151210
PCT Pub. Date: Aug. 8, 2019

(65) Prior Publication Data
US 2021/0113845 A1 Apr. 22, 2021

(30) Foreign Application Priority Data

Feb. 1, 2018 (JP) .............................. JP2018-016755

(51) Int. Cl.
*A61N 1/39* (2006.01)
(52) U.S. Cl.
CPC ......... *A61N 1/3968* (2013.01); *A61N 1/3956* (2013.01)
(58) Field of Classification Search
CPC ..... A61N 1/3968; A61N 1/3956; H01R 13/46
See application file for complete search history.

(56) References Cited

U.S. PATENT DOCUMENTS

| 2011/0160785 A1* | 6/2011 | Mori | A61N 1/0563 607/5 |
| 2011/0245895 A1* | 10/2011 | McGiboney | B23K 26/32 607/72 |
| 2017/0172652 A1* | 6/2017 | Govari | H01R 24/58 |

FOREIGN PATENT DOCUMENTS

| JP | 5-115567 A | | 5/1993 |
| JP | 2016087360 A | * | 5/2016 |

OTHER PUBLICATIONS

International Search Report, issued in PCT/JP2019/002880, dated Mar. 19, 2019.
(Continued)

*Primary Examiner* — Catherine M Voorhees
(74) *Attorney, Agent, or Firm* — Birch, Stewart, Kolasch & Birch, LLP

(57) ABSTRACT

A defibrillation system having a defibrillation catheter and a power supply part; a first connector member (11) is connected to a handle member; a second connector member (21) is connected to the power supply part; the first connector member (11) has a first insulating member (12), first electrodes (13) protruding from the first insulating member (12), and a first tubular member (14); the second connector member (21) has a second insulating member (22) having longitudinal holes, second electrodes (23) disposed on an inner wall of the longitudinal holes, and a second tubular member (24); the first tubular member (11) has a first space (15) being to contain the second tubular member (24), a second space (16) not containing the first insulating member (12) but containing the first electrodes (13), and a third space (17) containing neither the first insulating member (12) nor the first electrodes (13).

15 Claims, 6 Drawing Sheets

(56) References Cited

OTHER PUBLICATIONS

Written Opinion of the International Searching Authority, issued in PCT/JP2019/002880, dated Mar. 19, 2019.

\* cited by examiner

[Fig. 1]
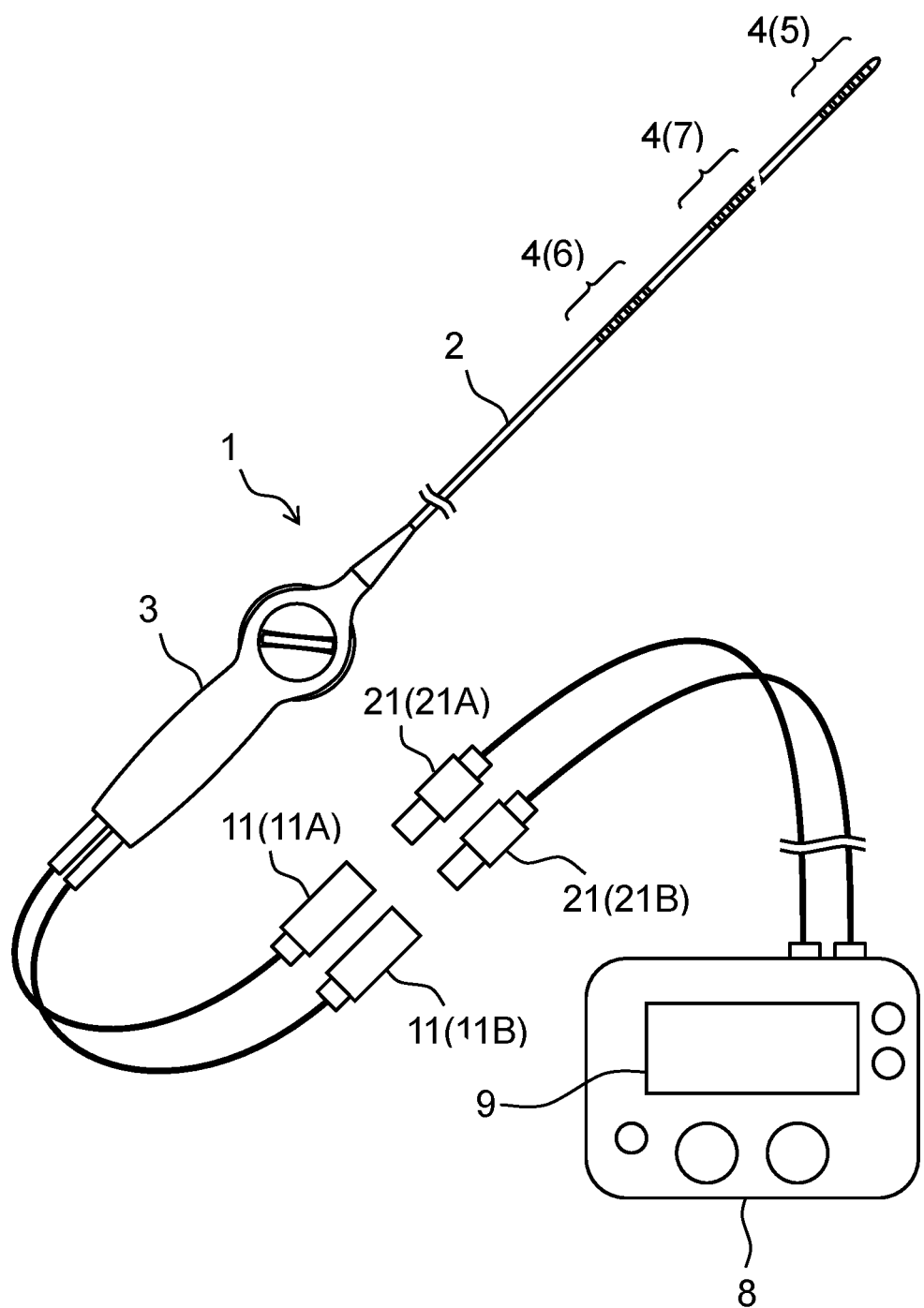

[Fig. 2]
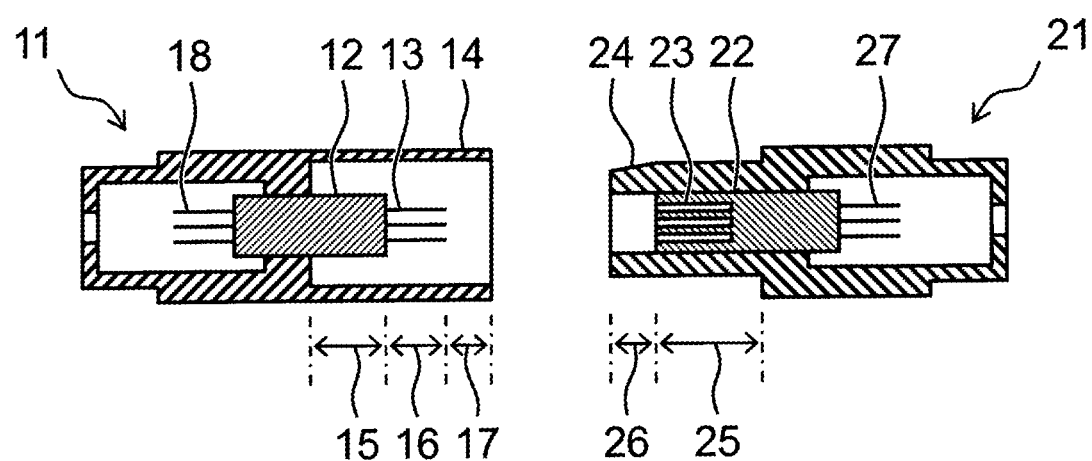
[Fig. 3]
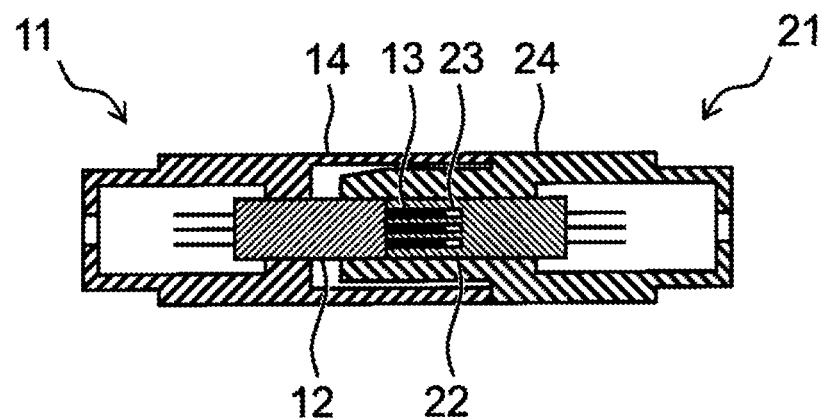

[Fig. 4]
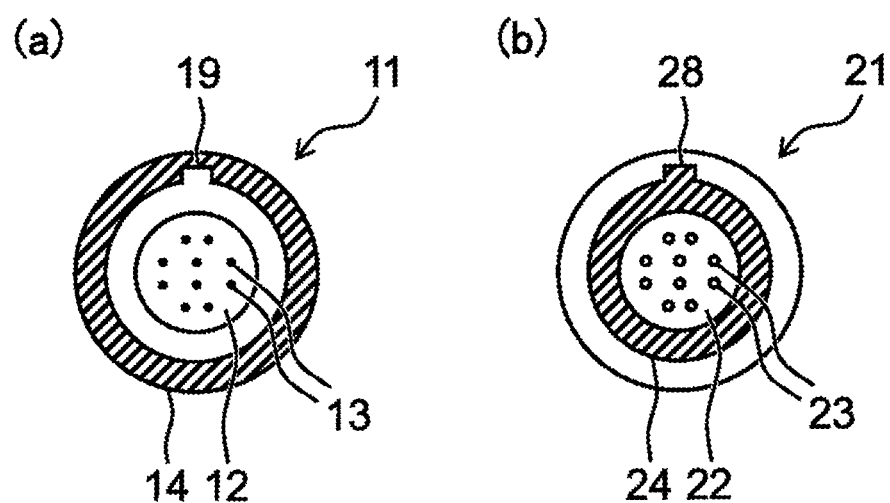

[Fig. 5]
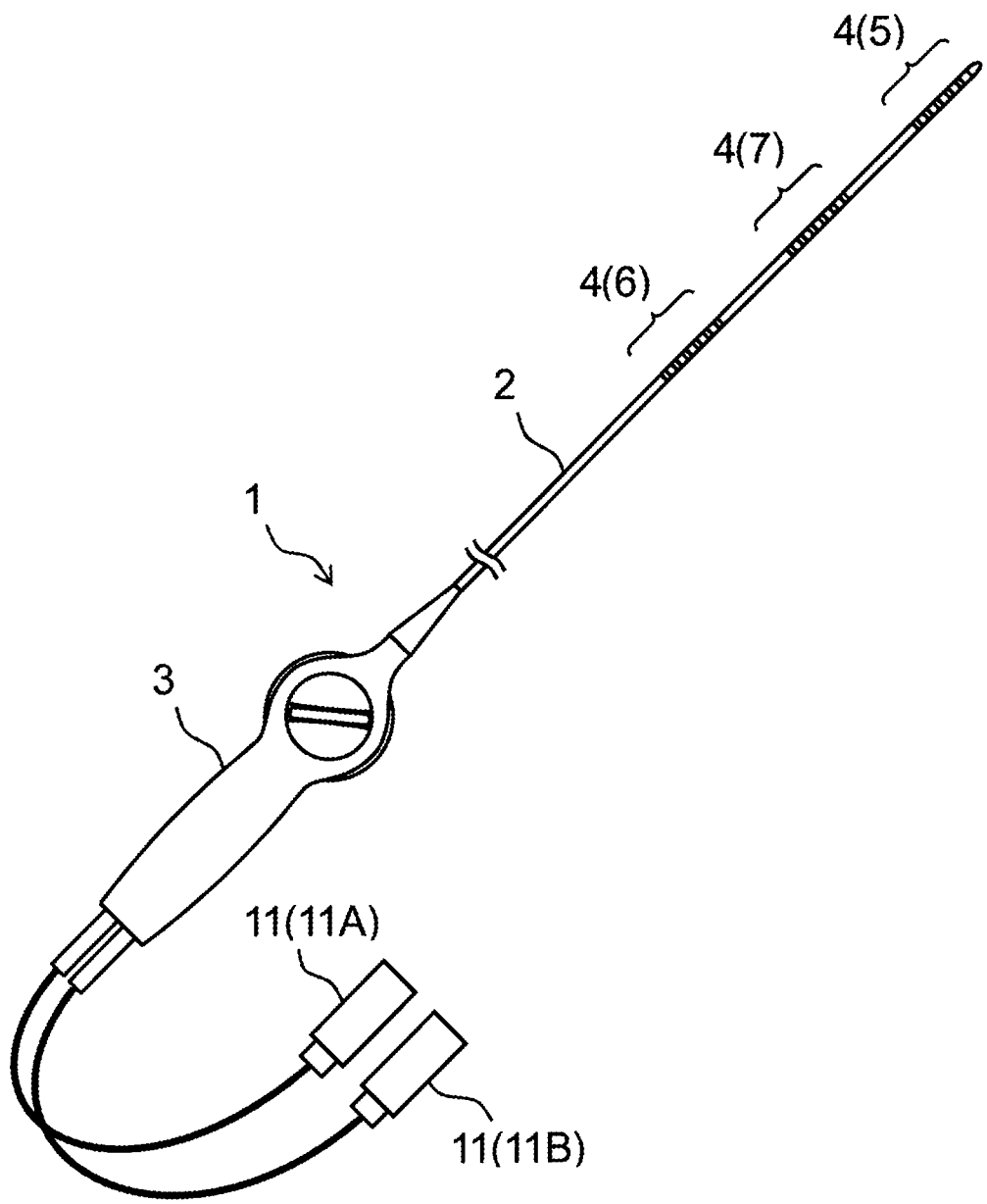

[Fig. 6]
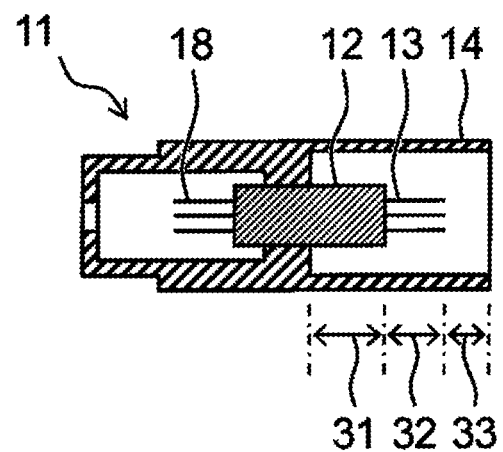

[Figure 7]
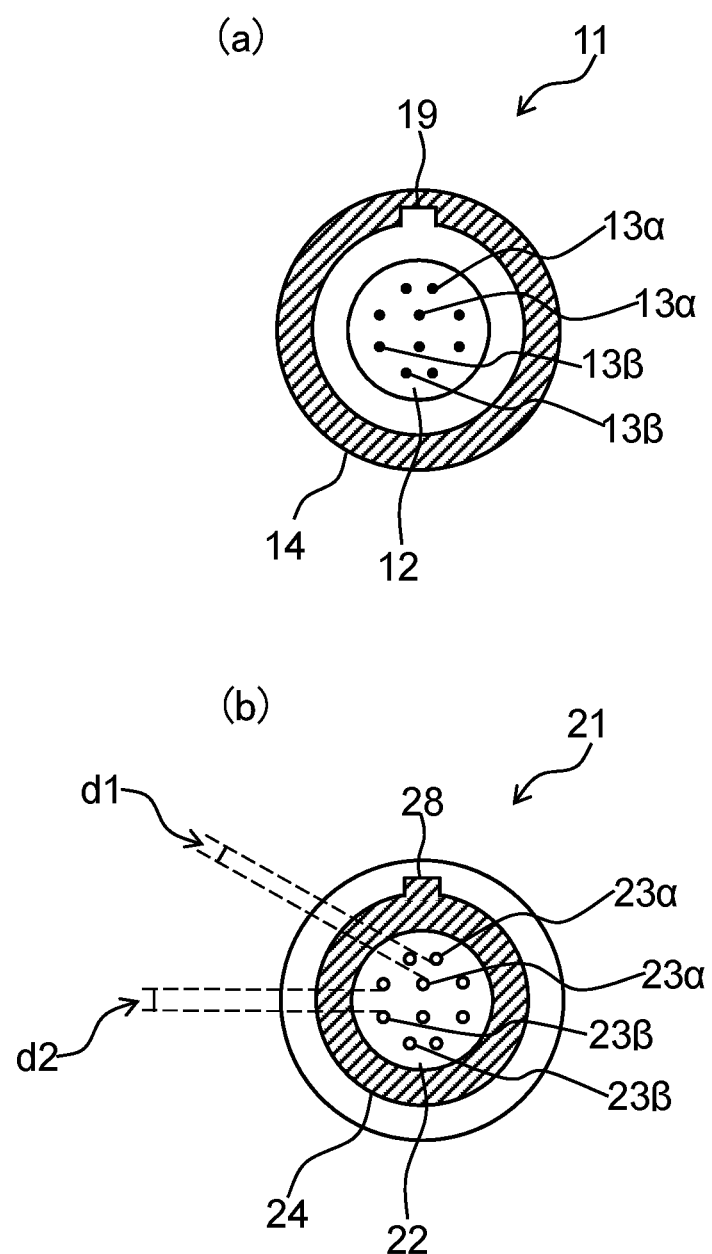

DEFIBRILLATION SYSTEM AND DEFIBRILLATION CATHETER

TECHNICAL FIELD

The present invention relates to a defibrillation system having a defibrillation catheter and a power supply part, and a defibrillation catheter.

BACKGROUND ART

To treat arrhythmia such as atrial fibrillation or ventricular fibrillation, defibrillation procedure, which restores the heart rhythm to normal by applying electric stimuli to the heart, was performed. For defibrillation procedure, Automated External Defibrillator (AED), Implantable Cardioverter Defibrillator (ICD), defibrillation paddle system, and defibrillation catheter system are used. Among them, the defibrillation catheter system has advantage over external defibrillators in that the defibrillation catheter system can use lower energy voltage waveform to alleviate a burden on a patient, and furthermore, the defibrillation catheter system can be used while a catheterization test of arrhythmia and an ablation surgery.

The defibrillation catheter system is generally composed of a system having a defibrillation catheter and a power supply part, in which intracardiac electrodes disposed on a distal side of the defibrillation catheter is electrically connected to the power supply part with conductive wires. The configuration enables a pulse voltage from the power supply part to be applied to a patient's heart through the intracardiac electrodes. For example, patent document 1 discloses a defibrillation system having an electric circuit connecting a defibrillation catheter and a power supply part. Specifically, the defibrillation catheter system disclosed in patent document 1 has main components of a flexible and insulated catheter body having a proximal end region and a distal end region, a distal end electrode, a bipolar ring electrode, a distal spring electrode, a proximal spring electrode, a distal tubular portion, a proximal tubular portion, a sheath containing the whole structure, and various kinds of conductive wires fulfilling overall functions.

RELATED ART DOCUMENT

Patent Document

Patent Document 1: JP-A-H05-115567

SUMMARY OF THE INVENTION

Problems to be Solved by the Invention

In a defibrillation procedure using a defibrillation catheter, which is performed in the condition where the catheter is electrically connected to a power supply part, a high voltage circuit of at most about 600 V is formed. Therefore, it is required for connecting the defibrillation catheter and the power supply part to ensure adequate safety. In realizing the above situation, the purpose of the present invention is to offer a defibrillation system having a defibrillation catheter and a power supply part, which enables the defibrillation catheter and the power supply part to be safely connected to each other.

Means for Solving the Problems

The defibrillation system of the present invention that can solve the aforementioned problem is a defibrillation system comprising: a defibrillation catheter having a handle member on a proximal side and at least one intracardiac electrode on a distal side; and a power supply part applying a pulse voltage to the defibrillation catheter, wherein the handle member is connected to a first connector member connected to the intracardiac electrode, and the power supply part is connected to a second connector member connected to the first connector member; the first connector member comprises a first insulating member, a plurality of first electrodes protruding from the first insulating member, and a first tubular member containing the first insulating member and the plurality of first electrodes; the second connector member comprises a second insulating member having a plurality of longitudinal holes, a plurality of second electrodes disposed on an inner wall of the plurality of longitudinal holes, and a second tubular member containing the second insulating member; the first tubular member has a first space, a second space, and a third space in this order from the side close to the handle member, wherein the first space is to contain at least a part of the second tubular member outside the first insulating member and inside the first tubular member; the second space does not contain the first insulating member but contains the first electrodes; and the third space contains neither the first insulating member nor the first electrodes.

The defibrillation system of the present invention enables the defibrillation catheter and the power supply part to be electrically connected each other by connecting the first connector member to the second connector member. The first connector member on the side of the catheter has the first space located at a position receded from the opening and the second space having a complicated structure including the plurality of first electrodes, both of which have such structures being relatively likely to get dusty. However, since the first connector member is connected to the handle member of the catheter, and is renewed with every catheter procedure, it is unlikely for the first space and the second space to get dusty while being used to ensure safety, even though the first space and the second space are formed in the first connector member. Since the first connector member further has the third space, finger tips of an operator are unlikely to touch the first electrodes to reduce risks that a patient's heart receives an electric shock such as static electricity. On the other hand, since the second connector member on the side of the power supply part has the second tubular member having a relatively simple structure, accumulation of dust on the second connector member associated with continuous use can be prevented or reduced in spite of repetitive use, and therefore, electric trouble caused by the dust is unlikely to occur Moreover, since the second connector member is configured such that the second electrodes are disposed in the inner wall of the longitudinal holes of the second insulating member, finger tips of an operator are unlikely to touch the second electrodes to prevent them from getting an electric shock. Accordingly, safety while connecting the first connector member to the second connector member can be improved.

The longitudinal holes of the second insulating member preferably have a part not having the second electrodes on an inner wall on the side close to the first insulating member.

In the condition where the first connector member is connected to the second connector member, the first insulating member of the first connector member and the second insulating member of the second connector member are preferably in contact with each other. In addition, in the condition where the first connector member is connected to the second connector member, an end of the first tubular member is preferably in contact with a part of the second connector member, and an end of the second tubular member of the second connector member is preferably not in contact with any part of the first connector member.

The second tubular member preferably has a second space containing the second insulating member and the second electrodes on the side of the power supply part, and has a third space contains neither the second insulating member nor the second electrodes. In this case, a length of the third space of the second tubular member in an axial direction is preferably shorter than a length of the third space of the first tubular member in an axial direction.

The defibrillation system is preferably configured such that the at least one intracardiac electrode comprises at least one intracardiac electrode A and at least one intracardiac electrode B; and the first connector member comprises a first connector member A connected to the intracardiac electrode A, and a first connector member B connected to the intracardiac electrode B; and the second connector member comprises a second connector member A connected to the first connector member A, and a second connector member B connected to the first connector member B. In this case, the defibrillation system is preferably configured such that the first connector member A is connected to the second connector member A, but is not connected to the second connector member B; and the first connector member B is connected to the second connector B, but is not connected to the second connector A.

The second connector member is preferably equipped with a disconnecting member for disconnecting the second connector member from the first connector member.

The defibrillation system may further comprise an electrocardiogram display that is connected to the power supply part and that transforms measured data by the defibrillation catheter into electrocardiogram. In this case, the plurality of second electrodes may comprise at least one second electrode $\alpha$ ($23\alpha$) that is connected to a power supply of the power supply part applying a pulse voltage to the defibrillation catheter and is connected to the electrocardiogram display, and at least one second electrode $\beta$ ($23\beta$) that is not connected to the power supply of the power supply part but is connected to the electrocardiogram display. A shortest distance among distance between the second electrode $\alpha$ and the second electrode $\beta$ (d2) is preferably longer than a shortest distance among distance between the second electrodes $\alpha$ (d1).

The present invention also provides a method of handling the aforementioned defibrillation system, comprising inserting the second connector member into the first connector member by advancing the second connector member toward the side of the first connector member while keeping the first connector member stationary.

The present invention further provides a defibrillation catheter, comprising a catheter tube extending in a distal-proximal direction, at least one intracardiac electrode disposed on a distal side of the catheter tube, a handle member disposed on a proximal side of the catheter tube, and a first connector member having one end connected to the intracardiac electrode through the handle member and another end connected to a power supply part, wherein the first connector member comprises a first insulating member, a plurality of first electrodes protruding from the first insulating member, and a first tubular member containing the first insulating member and the plurality of first electrodes; the first tubular member has a fourth space, a fifth space, and a sixth space in this order from the side close to the handle member, wherein the fourth space is located outside the first insulating member and inside the first tubular member, the fifth space does not contain the first insulating member but contains the first electrodes, and sixth space contains neither the first insulating member nor the first electrodes.

The defibrillation catheter is preferably configured such that the at least one intracardiac electrode comprises at least one intracardiac electrode A and at least one intracardiac electrode B, the first connector member comprises a first connector member A connected to the intracardiac electrode A and a first connector member B connected to the intracardiac electrode B. In this case, one part of the plurality of first electrodes preferably comprises at least one first electrode $\alpha$ ($13\alpha$) connected to the intracardiac electrode A or the intracardiac electrode B, and another part of the plurality of first electrodes comprises at least one first electrode $\beta$ ($13\beta$) connected to neither the intracardiac electrode A nor the intracardiac electrode B but connected to at least one intracardiac electrode C disposed on a distal side of the catheter tube.

Effects of the Invention

The defibrillation system and the defibrillation catheter of the present invention are configured such that the first connector member on the side of the catheter has the first space located at a position receded from the opening and the second space having a complicated structure including the plurality of first electrodes. Such spaces have a structure being relatively likely to get dusty, however, since the first connector member is connected to the handle member of the catheter, and is renewed with every catheter procedure, it is unlikely for the first space and the second space to get dusty while being used to ensure safety, even though the first space and the second space are formed in the first connector member. Furthermore, since the first connector member further has the third space, finger tips of an operator are unlikely to touch the first electrodes to reduce risks that a patient's heart receives an electric shock such as static electricity. On the other hand, since the second connector member on the side of the power supply part has the second tubular member having a relatively simple structure, accumulation of dust on the second connector member associated with continuous use can be prevented or reduced in spite of repetitive use, and therefore, electric trouble caused by the dust is unlikely to occur. Moreover, since the second connector member is configured such that the second electrodes are disposed in the inner wall of the longitudinal holes of the second insulating member, finger tips of an operator are unlikely to touch the second electrodes to prevent them from getting an electric shock. Accordingly, safety while connecting the first connector member to the corresponding connector member to electrically connect the defibrillation catheter to the power supply part can be improved.

BRIEF DESCRIPTION OF THE DRAWINGS

FIG. 1 is an overall view of a defibrillation system.

FIG. 2 is a cross-sectional view in the axial direction of a first connector member and a second connector member when they are not connected.

FIG. 3 is a cross-sectional view in the axial direction of a first connector member and a second connector member when they are connected.

FIG. 4 is a cross-sectional view orthogonal to the axial direction of a first connector member and a second connector member.

FIG. 5 is an overall view of a defibrillation catheter.

FIG. 6 is a cross-sectional view in the axial direction of a first connector member.

FIG. 7 is a cross-sectional view orthogonal to the axial direction of a first connector member and a second connector member of another embodiment.

MODE FOR CARRYING OUT THE INVENTION

The present invention relates to a defibrillation catheter and a defibrillation system including the defibrillation catheter. The defibrillation catheter, which is composed of a catheter tube equipped with at least one intracardiac electrode on a distal side, and a handle member disposed on a proximal side of the catheter tube, can be used for defibrillation procedure by delivering the catheter tube to a patient's heart through blood vessels and applying a pulse voltage to the intracardiac electrode. In the defibrillation system, the defibrillation catheter is electrically connected to a power supply part to apply a pulse voltage to the intracardiac electrode of the defibrillation catheter from the power supply part. High voltage circuit of at most about 600 V is formed in the defibrillation system, however, the defibrillation system of the present invention enables the defibrillation catheter and the power supply part to be connected safely.

Hereinafter, the defibrillation catheter and the defibrillation system according to the present invention will be described based on the following embodiments, however, the present invention is not limited by the following embodiments and can be altered in design within a scope in compliance with the intent described above and below, and all the changes are to be encompassed within a technical scope of the present invention. Note that, in each drawing, hatching, reference signs for components, and the like may be omitted for convenience of description, and in such a case, the specification and other drawings are to be referred to. Furthermore, since the dimensions of the various components in the drawings are provided for the purpose of facilitating the understanding of the feature of the present invention, the dimensions may differ from the actual dimensions in some cases.

Referring to FIG. 1, the overall defibrillation system will be described. FIG. 1 shows a schematic view of the defibrillation system including the defibrillation catheter and the power supply part.

A defibrillation catheter 1 has a catheter tube 2 and a handle member 3 disposed on a proximal side of the catheter tube 2. At least one intracardiac electrode 4 is disposed on a distal side of the catheter tube 2, and a conductive wire is disposed in the catheter tube 2. The defibrillation catheter 1 is used for defibrillation procedure for a heart by delivering the catheter tube 2 to a patient's heart through blood vessels. For the catheter and the defibrillation system, the proximal side is the side of a user's, that is an operator's hand, and the distal side is the opposite side to the proximal side, that is, the side of an object of the treatment.

The catheter tube 2 has a flexible and tubular structure and extends in the distal-proximal direction. The catheter tube 2 may be made of, for example, synthetic resin such as polyolefin resin (such as polyethylene and polypropylene), polyamide resin (such as nylon), polyester resin (such as PET), aromatic polyether ketone resin (such as PEEK), polyetherpolyamide resin, polyurethane resin, polyimide resin, and fluorine resin (such as PTFE, PFA, ETFE); and metals such as stainless steel, carbon steel, and nickel-titanium alloy. The length in the axial direction (the distal-proximal direction) of the catheter tube 2, which is a few times to several tens of times as long as the handle member 3 in the axial direction, is, for example, about 500 mm to 1200 mm. The outer diameter of the catheter tube 2 may be, for example, about 0.6 mm to 3 mm.

On the distal side of the catheter tube 2, the at least one intracardiac electrode 4 is disposed. The at least one intracardiac electrode 4 may be a plurality of intracardiac electrode 4, specifically, the at least one intracardiac electrode 4 may include at least one intracardiac electrode A and at least one intracardiac electrode B, which are for applying voltage, and may further include at least one intracardiac electrode C for measuring electrocardiogram. In the catheter 1 shown in FIG. 1, for example, a group of electrodes 5 on the distal side of the catheter tube 2 may be the intracardiac electrode A, and a group of electrodes 6 on the proximal side may be the intracardiac electrode B. Regarding the intracardiac electrode C, a group of electrodes 7 between the intracardiac electrode A and the intracardiac electrode B may be the intracardiac electrode C, or the intracardiac electrode A and/or the intracardiac electrode B may have a function for measuring electrocardiogram.

The intracardiac electrode 4 is made of, for example, metal materials such as copper, gold, platinum, aluminum, iron, and an alloy thereof. In order to make the catheter sensitive to radiographic visualization while being used, the intracardiac electrode 4 is preferably made of platinum or an alloy thereof.

The catheter tube 2, which has at least one lumen, may have a single lumen structure with one lumen therein, or may have a multi lumen structure with more than one lumens therein. In the lumen of the catheter tube 2, at least one conductive wire connected to the intracardiac electrode 4 disposed on the distal side of the catheter tube 2 is placed. The at least one conductive wire preferably comprises at least both a conductive wire A connected to the intracardiac electrode A and a conductive wire B connected to the intracardiac electrode B, each of which is disposed in the lumen of the catheter tube 2. The at least one conductive wire may be a group of conductive wires.

The handle member 3 is disposed on the proximal side of the catheter tube 2, and after being assembled as a catheter, the distal side of the conductive wire is connected to the intracardiac electrode 4 on the catheter tube 2, and the proximal side of the conductive wire is connected to a first connector member 11 through the handle member 3. And then, the first connector member 11 is connected to a second connector member 21 to electrically connect the intracardiac electrode to the power supply part and an electrocardiogram display.

The conductive wire, which just has to include at least a conductive material, may be made of, for example, iron wire, silver wire, stainless wire, copper wire, tungsten wire, or nickel titanium wire. The conductive wire preferably includes the conductive material as a core material covered by an insulating material. The insulating material may include fluorine resin (such as PTFE, PFA, FEP, and ETFE), polyolefin resin (such as polyethylene and polypropylene), polyvinyl chloride resin, and the like.

In the lumen of the catheter tube 2, at least one wire for bending the distal side of the catheter tube 2 is preferably placed. The at least one wire placed in the lumen of the catheter tube 2 may comprise a wire or a plurality of wires. The distal side of the wire is fixed to the catheter tube 2, for example, to a distal end portion of the catheter tube 2, and the proximal side of the wire is fixed to the handle member 3.

The at least one wire is placed to bend the distal side of the catheter tube 2. Pulling the wire by manipulating the handle member 3 enables the distal side of the catheter tube 2 to be bent. Alternatively, by pushing the wire to the distal side, the distal side of the catheter tube 2 can be bent. The wire may be a wire made of, for example, metal such as stainless steel, carbon steel, and nickel-titanium alloy; or synthetic resin such as polyamide resin (such as nylon), polyolefin resin (such as polyethylene and polypropylene), polyester resin (such as PET), aromatic polyether ketone resin (such as PEEK), polyimide resin, and fluorine resin (such as PTFE, PFA, FEP, and ETFE). The diameter of the wire may be, for example, about 100 μm to 500 μm. The wire may be covered by a cylindrical body made of coil-like metal or synthetic resin.

The defibrillation catheter 1 can be used by being connected to the power supply part 8 applying a voltage and connecting the intracardiac electrode 4 to a patient's heart. For example, by applying a pulse voltage of up to about 600 V between the intracardiac electrode A and the intracardiac electrode B, the defibrillation procedure can be performed. The power supply part 8 has a power supply for applying a pulse voltage to the defibrillation catheter 1, and the intracardiac electrode A and the intracardiac electrode B are connected to the power supply. The at least one intracardiac electrode A and the at least one intracardiac electrode B may be one electrode or a plurality of electrodes, but from the viewpoint of reducing impedance to perform efficient defibrillation procedure, the at least one intracardiac electrode A and the at least one intracardiac electrode B are preferably a plurality of electrodes. The intracardiac electrode A is connected to the conductive wire A, the intracardiac electrode B is connected to the conductive wire B, and the conductive wire A and the conductive wire B extend to the proximal side of the handle member 3 through the catheter tube 2.

In the case where an electrocardiogram display is connected to the catheter 1, intracardiac potential can be measured with the intracardiac electrode A, the intracardiac electrode B, and the intracardiac electrode C. The electrocardiogram display displays the intracardiac potential measured with the defibrillation catheter 1 as an intracardiac electrocardiogram. The at least one intracardiac electrode C may comprise an intracardiac electrode C or a plurality of intracardiac electrode C, but generally the at least one intracardiac electrode C is the plurality of intracardiac electrode C. The intracardiac electrode C is connected to a conductive wire C, and the conductive wire C extends to the proximal side of the handle member 3 through the catheter tube 2. In this case, the catheter 1 may be connected to the electrocardiogram display via the power supply part 8, or may be connected to the electrocardiogram display not via the power supply part 8. The defibrillation system including the electrocardiogram display can display the intracardiac potential measured with the intracardiac electrode 4 of the catheter 1 as an intracardiac electrocardiogram.

To the handle member 3, the first connector member 11 connected to the intracardiac electrode 4 is connected. In FIG. 1, a first connector member A 11A connected to the intracardiac electrode A and a first connector member B 11B connected to the intracardiac electrode B are connected to the handle member 3. The first connector member A 11A is connected to the intracardiac electrode A through the conductive wire A located in the catheter tube 2 and the handle member 3, and the first connector member B 11B is connected to the intracardiac electrode B through the conductive wire B located in the catheter tube 2 and the handle member 3. One end of the first connector member A 11A is connected to the intracardiac electrode A through the handle member 3, and another end of the first connector member A 11A is electrically connected to the power supply part 8; and one end of the first connector member B 11B is connected to the intracardiac electrode B through the handle member 3, and another end of the first connector member B 11B is electrically connected to the power supply part 8. Not shown in the figures, the first connector member 11 may comprise one first connector member, and in this case, the conductive wire A connected to the intracardiac electrode A and the conductive wire B connected to the intracardiac electrode B may be connected to the same first connector member 11. In the present specification, hereinafter, the first connector member A 11A and the first connector member B 11B may be collectively referred to as "first connector member". In addition, electrical "connecting" in the present invention includes both direct connecting and indirect connecting.

The first connector member 11 is configured such that the tubular member is equipped with a male connection terminal therein. The inner structure of the first connector member 11 will be specifically described referring to FIG. 2. FIG. 2 shows a cross-sectional view in the axial direction of the first connector member and the after-mentioned second connector member. In FIG. 2, the right side of the figure is the side of the power supply part 8, which is the proximal side, and the left side of the figure is the side of the handle member 3, which is the distal side.

The first connector member 11 has a first insulating member 12, a plurality of first electrodes 13 protruding from the first insulating member 12, and a first tubular member 14 containing the first insulating member 12 and the plurality of first electrodes 13. The insulating member 12 is a base member from which the first electrodes protrude, and may be made of insulating materials such as ceramics and plastics. The first electrodes 13 are formed to have a pin-like shape protruding from the first insulating member 12 to at least the proximal side, and may be made of metal materials such as copper, gold, platinum, aluminum, iron, and an alloy thereof. The first electrodes 13 are electrically connected to the intracardiac electrode 4 through the conductive wire. In FIG. 2, the first electrodes 13 are disposed so as to pierce through the first insulating member 12 in the axial direction of the first tubular member 14, and to protrude from the first insulating member 12 to also the distal side. The first electrodes 13 protruding from the first insulating member 12 to the distal side behave as a connection terminal 18. The first tubular member 14 is a member protecting the first electrodes 13, and has a tubular shape. The first tubular member 14 is configured such that the axial direction of the tubular shape is approximately parallel to the extending direction of the first electrodes 13, and a peripheral wall of the first tubular member 14 is formed to encircle the axis of the tubular shape. The first tubular member 14 may be made of insulating materials such as ceramics and plastics. The first insulating member 12 and the first electrodes 13 are disposed to be located more distal than the proximal end of the first tubular member 14, thereby the first insulating member and the first electrodes 13 are contained in the first tubular member 14.

The first connector member 11 having the aforementioned configuration enables an operator to safely connect or disconnect the first connector member 11 and the after-mentioned second connector member 21, holding the first tubular member 14 without touching the first electrodes 13. In addition, while the first connector member 11 is configured such that the plurality of first electrodes 13 protrude from the first insulating member 12, high voltage is not applied to the first electrodes 13 in the condition where the first electrodes 13 is not connected to the second connector member 21 to be exposed. Therefore, if finger tips or the like of an operator touch the first electrodes 13, which may lead to risk of electric shock to the operator, the risk can be prevented or reduced.

The first connector member 11 may be configured such that, for example, the relative permittivity of the first tubular member 14 is lower than the relative permittivity of the first insulating member 12, which can prevent or reduce mutual induction to reduce mutual electromagnetic effect. On the contrary, the first connector member 11 may be configured such that the relative permittivity of the first insulating member 12 is lower than the relative permittivity of the first tubular member 14, and for example, in the case where heteropolar electrodes are disposed in the first connector member 11, the first insulating member 12 preferably has higher insulation properties, that is, the first insulating member 12 has lower relative permittivity.

The first connector member 11 is equipped with the plurality of first electrodes 13, and one part of the plurality of first electrodes 13 may comprises at least one first electrode α connected to the intracardiac electrode A or the intracardiac electrode B, which is for applying voltage, and another part of the plurality of first electrodes 13 may comprises at least one first electrode β connected to neither the intracardiac electrode A nor the intracardiac electrode B but connected to the intracardiac electrode C for measuring electrocardiogram. Such a configuration of the first electrodes 13 enables electrocardiogram measurement along with defibrillation procedure, and furthermore, electrocardiogram measurement and defibrillation procedure can be simultaneously performed. In this case, each of the first connector member A 11A and the first connector member B 11B may be equipped with the first electrode α and the first electrode β. Note that if the intracardiac electrode A or the intracardiac electrode B also performs as the electrode for measuring electrocardiogram, the first connector member 11 may be configured such that the first electrode α is connected to the intracardiac electrode A or the intracardiac electrode B, and the first electrode β is also connected to the intracardiac electrode A or the intracardiac electrode B.

The first connector member 11 is preferably configured such that the shortest distance among distance between the first electrode α and the first electrode β is longer than the shortest distance among distance between the first electrodes α. The first electrode β for measuring electrocardiogram disposed apart from the first electrode α for applying voltage by a certain distance can prevent a leak from the first electrode α to the first electrode β to improve safety.

The defibrillation system is configured such that the first connector member 11 is connected to the second connector 21, and the second connector 21 is connected to the power supply part 8. In FIG. 1, the first connector member A 11A is connected to a second connector member A 21A, the first connector member B 11B is connected to a second connector member B 21B, and each of the second connector member A 21A and the second connector member B 21B is connected to the power supply part 8. Accordingly, to the power supply part 8, the second connector member A 21A connected to the first connector member A 11A and the second connector member B 21B connected to the first connector member B 11B are to be connected. Thereby, a pulse voltage from the power supply part 8 can be applied to the intracardiac electrode A through the second connector member A 21A and the first connector member A 11A, and also to the intracardiac electrode B through the second connector member B 21B and the first connector member B 11B. Note that the second connector member A 21A and the second connector member B 21B may be collectively referred to as "second connector member".

The second connector member 21 is configured such that the tubular member is equipped with a female connection terminal therein. Specifically, as shown in FIG. 2, the second connector member 21 has a second insulating member 22 having a plurality of longitudinal holes, a plurality of second electrodes 23 disposed on an inner wall of the plurality of longitudinal holes, and a second tubular member 24 containing the second insulating member 22. The second insulating member 22 is a base member for forming the second electrodes 23 having a longitudinal hole-like shape, and may be made of insulating materials such as ceramics and plastics. In the second insulating member 22, the plurality of longitudinal holes are formed so as to extend from the distal end to the proximal side of the second insulating member 22. The second electrodes 23 are formed on the inner wall of the longitudinal holes, and may be made of metal materials such as copper, gold, platinum, aluminum, iron, and an alloy thereof. The second electrodes 23 are electrically connected to the power supply part 8 through conductive wires and the like. In FIG. 2, a connection terminal 27 is disposed that is connected to the second electrodes 23 in the second insulating member 22 and protruding from the second insulating member 22 to the proximal side, and the conductive wire connected to the power supply part 8 is connected to the connection terminal 27. The second tubular member 24 is a member protecting the second electrodes 23 and the second insulating member 22, and has a tubular shape. The second tubular member 24 is configured such that the axial direction of the tubular shape is approximately parallel to the extending direction of the longitudinal holes in which the second electrodes 23 are formed, and a peripheral wall of the second tubular member 24 is formed to encircle the axis of the tubular shape. The second tubular member 24 may be made of insulating materials such as ceramics and plastics. The second insulating member 22 is disposed to be located more proximal than the distal end of the second tubular member 24, thereby the second insulating member 22 is contained in the second tubular member 24.

The second connector member 21 having the aforementioned configuration enables an operator to safely connect or disconnect with the first connector member 11, holding the second tubular member 24 without touching the second electrodes 23 and the second insulating member 22. Especially, while the second connector member 21 is required to be highly safe because the second connector member 21 is connected to the power supply part 8, if finger tips and the like of an operator touch the second insulating member 22, it is unlikely for them to further touch the second electrodes 23. In addition, it becomes easy to secure creepage distance between adjacent second electrodes 23 in the second connector member 21. From the viewpoint of further making it difficult for fingers and the like of an operator to touch the second electrodes 23 and securing longer creepage distance between adjacent second electrodes 23, the longitudinal holes of the second insulating member 22 is preferably have a part not having the second electrodes 23 in the inner all on the side close to the first insulating member 12, that is the distal side of the longitudinal holes. For example, in a preferable embodiment, the second electrodes 23 are not formed in the range of 0.5 mm from the opening of the longitudinal holes of the second insulating member 22.

The second connector member 21, for example, may be configured such that the relative permittivity of the second tubular member 24 is lower that the relative permittivity of the second insulating member 22, which can prevent or reduce mutual induction to reduce mutual electromagnetic effect. On the contrary, the second connector member 21 may be configured such that the relative permittivity of the second insulating member 22 is lower than the relative permittivity of the second tubular member 24, and for example, in the case where heteropolar electrodes are disposed in the second connector member 21, the second insulating member 22 preferably has higher insulation properties, that is, the second insulating member 22 has lower relative permittivity.

The second electrodes 23 may be comprise at least one second electrode α that is connected to the power supply applying a pulse voltage of the power supply part 8 and also connected to the electrocardiogram display, and at least one second electrode β that is not connected to the power supply applying a pulse voltage but is connected to the electrocardiogram display. In this case, when the first connector member 11 and the second connector member 12 are connected to each other, the second electrode α is to be connected to the first electrode α, and the second electrode β is to be connected to the first electrode β. In this case, each of the second connector A 21A and the second connector B 21B may be comprise the at least one second electrode α and the at least one second electrode β. The second electrode having such a configuration enables the catheter 1 to be used for electrocardiogram measurement as well as defibrillation procedure.

The second electrode β may be connected to the electrocardiogram display via the power supply part 8, or be connected to the electrocardiogram display not via the power supply part 8. In the former case, the second electrode β is connected to the power supply part 8 as well as the second electrode α, and the power supply part 8 is connected to the electrocardiogram display, which makes it possible for an electric signal from the second electrode β to be input to the electrocardiogram display via the power supply part 8. In the latter case, at least one conductive wire connected to the second electrode α and at least one conductive wire connected to the second electrode β are separately disposed from the second connector member, and the electrode connected to the second electrode α is to be connected to the power supply part 8 and the electrode connected to the second electrode β is to be connected to the electrocardiogram display. In this case, the second electrode β is not connected to the power supply part, but connected to the electrocardiogram display. In the case where the second electrode β is connected to the electrocardiogram display via the power supply part 8, the configuration is preferable that the second electrode β is not connected to the power supply applying a pulse voltage of the power supply part 8. Connecting the second electrode α to the power supply of the power supply part 8 and also to the electrocardiogram display makes it possible for an electrode corresponds to the second electrode α to be used for electrocardiogram measurement.

In the case where the second electrodes 23 comprise the second electrode α and the second electrode β, the shortest distance among distance between the second electrode α and the second electrode β is preferably longer than a shortest distance among distance between the second electrodes α. Disposing the second electrode β for electrocardiogram measurement apart from the second electrode α for applying voltage by a certain distance can secure creepage distance, which can prevent a leak from the second electrode α to the second electrode β to improve safety.

When using the catheter 1, the second connector member 21 is connected to the first connector member 11, during which at least a part of the second connector member 21 is placed in the first tubular member 14 of the first connector member 11. The defibrillation system shown in FIG. 1, the second connector member A 21A is connected to the first connector member A 11A, and the second connector member B 21B is connected to the first connector member B 11B, during which at least a part of the second connector member A 21A is placed in the first tubular member 14 of the first connector member A 11A, and at least a part of the second connector member B 21B is placed in the first tubular member 14 of the first connector member B 11B. The method for connecting the first connector member 11 and the second connector member 21 will be specifically described referring to FIG. 2 and FIG. 3. FIG. 2 shows a cross-sectional view in the axial direction of the first connector member and the second connector member when they are not connected, and FIG. 3 shows a cross-sectional view in the axial direction of the first connector member and the second connector member when they are connected. In FIG. 2 and FIG. 3, the right side of the figure is the proximal side, which is the side of the power supply part 8, and the left side of the figure is the distal side, which is the side of the handle member 3.

The first tubular member 3 of the first connector member 11 is configured so as to have a first space 15, a second space 16, and a third space 17 in this order from the side close to the handle member: the first space 15 is to contain at least a part of the second tubular member 24 outside the first insulating member 12 and inside the first tubular member 14; the second space 16 does not contain the first insulating member 12 but contains the first electrodes 13; and the third space 17 contains neither the first insulating member 12 nor the first electrodes 13. Configuring the first connector member 11 in such a way can improve safety of the defibrillation system. The reason is the following: the first space 15 is located at a position receded from the opening of the first connector member 11, and the second space 16 has a complicated structure including the plurality of first electrodes 13, both of which have such structures being relatively likely to get dusty, however, since the first connector member 11 is connected to the handle member 13 and is renewed with every catheter procedure, it is unlikely for the first space 15 and the second space 16 to get dusty while being used to ensure safety, even though the first space 15 and the second space 16 are formed in the first connector member 11. Since the first connector member 11 further has the third space 17, finger tips of an operator are unlikely to touch the first electrodes 13 to reduce risks that a patient's heart receives an electric shock such as static electricity. On the other hand, since the second connector member 21 on the side of the power supply part 8 has the second tubular member 24 having a relatively simple structure, accumulation of dust on the second connector member 21 associated with continuous use can be prevented or reduced in spite of repetitive use, and therefore, electric trouble caused by the dust is unlikely to occur. The first space 15 of the first connector member 11 is, to keep dust from entering, preferably configured such that the distance between the outer side of the first insulating member 12 and the inner side of the first tubular member 14 is to be narrow to some extent, and for example, the distance is preferably 5 mm or less, more preferably 3 mm or less.

The second connector member 21 is preferably configured such that the second tubular member 24 has a second space 25 containing the second insulating member 22 and the second electrodes 23 on the side of the power supply part 8 (the proximal side), and has a third space 26 containing neither the second insulating member 22 nor the second electrodes 23 on the side of the handle member 3 (the distal side). Due to such a configuration in which the third space 26 is formed in the second tubular member 24 of the second connector member 21, an operator's finger tips and the like are unlikely to touch the second insulating member 22 to improve safety while operating the second connector member 21. Note that while the first tubular member 14 of the first connector member 11 has the first space 15 for containing the second tubular member 24, the second tubular member 24 of the second connector member 21 does not have a space for containing the first tubular member 14.

A length of the third space 26 of the second tubular member 24 of the second connector member 21 in an axial direction is shorter than a length of the third space 17 of the first tubular member 14 of the first connector member 11 in an axial direction. Since the second tubular member 24 has smaller inner diameter relative to the first tubular member 14, an operator's finger tips and the like are unlikely to go into the second tubular member 24, and therefore, even shorter length of the third space 26 of the second tubular member 24 that is not as long as the third space 17 of the first tubular member 14 can reduce risks that an operator's fingers touch the second insulating member 22. Accordingly, the shorter length of the third space 26 of the second tubular member 24 enables the second connector member 21 to be formed compactly. On the other hand, longer length of the third space 17 of the first tubular member 14 in the axial direction can make it unlikely for an operator's fingers to touch the first electrodes 13 to improve safety for a patient while operating the first connector member 11. In addition, the shorter length of the third space 26 of the second tubular member 24 enables the first space 15 and the second space 16 of the first tubular member 14 to be formed with shorter length, and the whole structure of the connector can be formed compactly.

In the condition where the first connector member 11 and the second connector member 21 are connected to each other, the end side (the distal side) of the second tubular member 24 of the second connector member 21 is placed in the first space 15 of the first connector member 11, and at least a part of the first insulating member 12 of the first connector member 11 is placed in the third space 26 of the second connector member 21. On this occasion, a part of the first electrodes 13 of the first connector member 11 may be placed in the third space 26 of the second connector member 21. Note that both the second insulating member 22 and the second electrodes 23 are not placed in the first space 15 of the first connector member 11. In the second space 16 of the first connector member 11, the second insulating member 22 and at least a part of the second electrodes 23 are placed along with a part of the second tubular member 24. The second space 25 of the second connector member 21 contains the second insulating member 22 having the longitudinal holes, in which the second electrodes 23 are formed, and the first electrodes 13 of the first connector member 11 are inserted into the longitudinal holes. The third space 17 of the first connector member 11 may contain a part of the second tubular member 24, and may further contain the second insulating member 22 and a part of the second electrodes 23.

In the condition where the first connector member 11 is connected to the second connector member 21, the first insulating member 12 of the first connector member 11 and the second insulating member 22 of the second connector member 21 are preferably in contact with each other (see FIG. 3). Specifically, connection of the first connector member A 11A to the second connector member A 21A is preferably in such a manner, and connection of the first connector member B 11B to the second connector member B 21B is preferably in such a manner. The first insulating member 12 of the first connector member 11 and the second insulating member 22 of the second connector member 21 being in contact with each other can eliminate a part where insulating member does not exist between the electrodes to secure creepage distance. Thereby, risks of electric leakage can be reduced.

In addition, in the condition where the first connector member 11 is connected to the second connector member 21, the first connector member 11 and the second connector member 21 are preferably configured such that the end (the proximal end) of the first tubular member 14 of the first connector member 11 is in contact with a part of the second connector member 21, and the end (the distal end) of the second tubular member 24 of the second connector member 21 is not in contact with any part of the first connector member 11. Specifically, connection of the first connector member A 11A to the second connector member A 21A is preferably in such a manner, and connection of the first connector member B 11B to the second connector member B 21B is preferably in such a manner. In FIG. 2 and FIG. 3, the outer diameter of the second tubular member 24 of the second connector member 21 is formed to increase at a proximal side apart from the end (the distal end) of the second tubular member 24 by a predetermined length, thereby the end of the first tubular member 14 of the first connector member 11 is in contact with a part of the second tubular member 24 of the second connector member 21 when the first connector member 11 and the second connector member 21 are connected to each other. The connection between the first connector member 11 and the second connector member 21 in such a manner can prevent or reduce the entrance of dust or liquid into both the first tubular member 14 and the second tubular member 24 to further improve safety of the connection between the first electrodes 13 and the second electrodes 23.

The first connector member 11 and the second connector member 21 are preferably configured so as to fit into each other in a vertical cross-section in the axial direction. Specifically, the first connector member A 11A and the second connector member A 21A are preferably configured in such a manner, and the first connector member B 11B and the second connector member B 21B are preferably configured in such a manner. Thereby, when the first connector member 11 and the second connector member 21 are connected to each other, the first electrodes 13 can be connected to an appropriate position of the second electrodes 23. For example, the first connector member 11 and the second connector member 21 are preferably configured such that the inner side of the first tubular member 14 of the first connector member 11 and the outer side of the second tubular member 24 of the second connector member 21 fit into each other in a vertical cross-section in the axial direction.

FIG. 4(a) shows an example of a vertical cross-section view of the third space of the first connector member, and FIG. 4(b) shows an example of a vertical cross-section view of the third space of the second connector member. As shown in FIG. 4, a recessed groove 19 extending in the axial direction of the first tubular member 14 is formed on the inner side of the first tubular member 14 of the first connector member 11, and a ridge 28 extending in the axial direction of the second tubular member 24 is formed on the outer side of the second tubular member 24 of the second connector member 21. The ridge 28 is formed on the position corresponding to the recessed groove 19 when the second tubular member 24 is inserted into the first tubular member 14. The recessed groove 19 is formed so as to extend from the proximal end of the first tubular member 14 to the distal side. Such a configuration of the first connector member 11 and the second connector member 21 enables the ridge 28 to fit into the recessed groove 19 to connect the first connector member 11 with the second connector member 21 at an appropriate position when the second tubular member 24 is inserted into the first tubular member 14. Alternatively, a ridge may be formed on the inner side of the first tubular member 14 of the first connector member 11, and a recessed groove may be formed on the outer side of the second tubular member 24 of the second connector member 21. Such an alternative configuration also enables the first connector member 11 and the second connector member 21 to be connected to each other at an appropriate position.

The first connector member 11 and the second connector member 21 is preferably configured such that the second tubular member 24 is inserted to an predetermined position of the first tubular member 14 to engage with each other. Specifically, the first connector member A 11A and the second connector member A 21A are preferably configured in such a manner, and the first connector member B 11B and the second connector member B 21B are preferably configured in such a manner. Thereby, the first connector member 11 and the second connector member 21 can be stably connected to each other. For example, a ridge that can be pressed may be formed on the inner side of the first tubular member 14 of the first connector member 11, and a recessed groove may be formed on the outer side of the second tubular member 24 of the second connector member 21, so that the ridge on the inner side of the first tubular member 14 can be fit into the recessed groove on the outer side of the second tubular member 24 when the second tubular member 24 is inserted to a predetermined position of the first tubular member 14. Alternatively, a ridge that can be pressed may be formed on the outer side of the second tubular member 24 of the second connector member 21, and a recessed groove may be formed on the inner side of the first tubular member 14 of the first connector member 11. The recessed groove is formed on a position apart from the end of the first tubular member 14 or the second tubular member 24.

The ridge formed in the aforementioned manner can be pressed in the opposite direction to the protruding direction to break engagement with the recessed groove, so that connection between the first connector member 11 and the second connector member 21 can be broken. Such a ridge can be made possible to be pressed by being combined with spring mechanism, which can perform as a disconnecting member. Note that the disconnecting member is preferably formed on the second connector member 21, which is repetitive used, rather than on the first connector member 11, which is renewed with every catheter procedure, and thereby costs of the defibrillation catheter can be reduced.

As shown in FIG. 1, in the case where the first connector member 11 comprises the first connector member A 11A and the first connector member B 11B, and the second connector member 21 comprises the second connector member A 21A and the second connector member B 21B, the first connector member A 11A is preferably connected to the second connector member A 21A but not connected to the second connector member B 21B, and the first connector member B 11B is preferably connected to the second connector member B 21B but not connected to the second connector member A 21A. Such a configuration of each of the connector members can prevent each of the connector members from improperly connecting to each other. To form such a structure that can prevent improper connection, the end side (the distal side) of the second tubular member 24 of the second connector member A 21A just has shape and size capable of being contained in the first space 15 of the first connector member A 11A but not capable of being contained in the first space 15 of the first connector member B 11B, and the end side (the distal side) of the second tubular member 24 of the second connector member B 21B just has shape and size capable of being contained in the first space 15 of the first connector member B 11B but not capable of being contained in the first space 15 of the first connector member A 11A. For example, the vertical cross-section shape in the axial direction of each of the second tubular member 24 of the second connector member A 21A and the second connector member B 21B may be formed so as to correspond to the vertical cross-section shape in the axial direction of each of the first space 15 of the first connector member A 11A and the first connector member B 11B respectively.

An example of the structure that can prevent improper connection will be described exemplifying an embodiment shown in FIG. 4. For example, one recessed groove 19 may be formed on the inner side of the first tubular member 14 of the first connector member A 11A and one ridge 28 may be formed on the outer side of the second tubular member 24 of the second connector member A 21A, and on the other hand, two recessed grooves 19 may be formed on the inner side of the first tubular member 14 of the first connector member B 11B and two ridges 28 may be formed on the outer side of the second tubular member 24 of the second connector member B 21B, thereby improper connection between the each connector members can be prevented. Alternatively, the recessed groove 19 may be formed on the inner side of the first tubular member 14 of the first connector member A 11A and the ridge 28 may be formed on the outer side of the second tubular member 24 of the second connector member A 21A, and on the other hand, a ridge may be formed on the inner side of the first tubular member 14 of the first connector member B 11B and a recessed groove may be formed on the outer side of the second tubular member 24 of the second connector member B 21B (not shown in the figures), in order to prevent improper connection between the each connector members thereby.

The aforementioned defibrillation system in which the defibrillation catheter 1 is connected to the first connector member 11 and the power supply part 8 is connected to the second connector member 21 is preferably configured such that the first connector member 11 is connected to the second connector member 21 in the following manner. The second connector member 21 is preferably inserted into the first connector member 11 by advancing the second connector member 21 toward the side of the first connector member 11 while keeping the first connector member 11 stationary. In the embodiment shown in FIG. 1, the second connector member A 21A is preferably inserted into the first connector member A 11A by advancing the second connector member A 21A toward the side of the first connector member A 11A while keeping the first connector member A 11A stationary, and the second connector member B 21B is preferably inserted into the first connector member B 11B by advancing the second connector member B 21B toward the side of the first connector member B 11B while keeping the first connector member B 11B stationary. Thereby, when the first connector member 11 and the second connector member 21 are connected to each other, risks that the catheter 1 inserted into an patient's body might be tugged can be reduced to improve safety of handling the catheter 1.

The present invention also provides a defibrillation catheter having the first connector member. The defibrillation catheter of the present invention will be described referring to FIG. 5 and FIG. 6. FIG. 5 shows a schematic view of a defibrillation catheter, and FIG. 6 shows a cross-sectional view in the axial direction of the first connector member. Note that in FIG. 5 and FIG. 6, the same members and portions as in FIG. 1 to FIG. 4 are shown with the same reference signs, and hereinafter, detailed explanation of which will be omitted.

A defibrillation catheter 1 comprises a catheter tube 2 extending in a distal-proximal direction, at least one intracardiac electrode 4 disposed on a distal side of the catheter tube 2, a handle member 3 disposed on a proximal side of the catheter tube 2, and a first connector member 11 having one end connected to the intracardiac electrode 4 through the handle member 3 and another end connected to a power supply part 8. In FIG. 5, the intracardiac electrode 4 comprises an intracardiac electrode A and an intracardiac electrode B, and the first connector member 11 comprises a first connector member A 11A and a first connector member B 11B; and one end of the first connector member A 11A is connected to the intracardiac electrode A through the handle member 3 and another end of the first connector member A 11A is connected to the power supply part, and one end of the first connector member B 11B is connected to the intracardiac electrode B through the handle member 3 and another end of the first connector member B 11B is connected to the power supply part. The first connector member 11 comprises a first insulating member 12, a plurality of first electrodes 13 protruding from the first insulating member 12, a first tubular member 14 containing the first insulating member 12 and the plurality of first electrodes 13, and the first tubular member 14 has a fourth space 31, a fifth space 32, and a sixth space 33 in this order from the side close to the handle member 3, wherein the fourth space 31 located outside the first insulating member 12 and inside the first tubular member 14, the fifth space 32 does not contain the first insulating member 12 but contains the first electrodes 13, and the sixth space 33 contains neither the first insulating member 12 nor the first electrodes 13.

The first connector member 11 configured in the aforementioned manner can improve safety of connection between the first connector member 11 and a connector member on the side of the power supply part. The reason is the following: the fourth space 31 is located at a position receded from the opening of the first connector member 11, and the fifth space 32 has a complicated structure including the plurality of first electrodes 13, both of which have such structures being relatively likely to get dusty, however, since the first connector member 11 is connected to the handle member 3 and is renewed with every catheter procedure, it is unlikely for the fourth space 31 and the fifth space 32 to get dusty while being used to ensure safety, even though the fourth space 31 and the fifth space 32 are formed in the first connector member 11. In addition, since the first connector member 11 further has the sixth space 33, finger tips of an operator are unlikely to touch the first electrodes 13 to reduce risks that a patient's heart receives an electric shock such as static electricity. The fourth space 31 of the first connector member 11 is, to keep dust from entering, preferably configured such that the distance between the outer side of the first insulating member 12 and the inner side of the first tubular member 14 is to be narrow to some extent, and for example, the distance is preferably 5 mm or less, more preferably 3 mm or less.

The defibrillation system and the defibrillation catheter of the present invention have been described above, however, the first connector member 11 is not limited to the embodiment shown FIG. 1 and FIG. 5 in which the first connector member 11 comprises the first connector member A 11A and the first connector member B 11B, and may comprise only one first connector member 11. Corresponding to this, the second connector member 21 may comprise only one second connector member 21. In this case, the first connector member 11 is connected to the intracardiac electrode A and the intracardiac electrode B, and specifically, one part of the plurality of first electrodes 13 of the first connector member 11 is connected to the intracardiac electrode A and another part of the plurality of first electrodes 13 of the first connector member 11 is connected to the intracardiac electrode B. That is, heteropolar electrodes are disposed in the first connector member 11, and heteropolar electrodes are disposed in the second connector member 21.

The present application claims priority based on Japanese Patent Application No. 2018-016755 filed on Feb. 1, 2018. All the contents described in Japanese Patent Application No. 2018-016755 filed on Feb. 1, 2018 are incorporated herein by reference.

DESCRIPTION OF REFERENCE SIGNS

1: defibrillation catheter
2: catheter tube
3: handle member
4: intracardiac electrode
5: intracardiac electrode A
6: intracardiac electrode B
7: intracardiac electrode C
8: power supply part
9: electrocardiogram display
11: first connector member, 11A: first connector member A, 11B: first connector member B
12: first insulating member
13: first electrode
14: first tubular member
15: first space in the first tubular member
16: second space in the first tubular member
17: third space in the first tubular member
18: connection terminal of the first connector member
19: recessed groove
21: second connector member, 21A: second connector member B, 21B: second connector member B
22: second insulating member
23: second electrode
24: second tubular member
25: second space in the second tubular member
26: third space in the second tubular member
27: connection terminal of the second connector member
28: ridge
31: fourth space in the first tubular member
32: fifth space in the first tubular member
33: sixth space in the first tubular member

The invention claimed is:
1. A defibrillation system comprising:
a defibrillation catheter having a handle member on a proximal side and at least one intracardiac electrode on a distal side,
a power supply part for applying a pulse voltage to the defibrillation catheter,
a handle member, a first connector member, and
a second connector member;
  the power supply part connected to the second connector member to be connected to the first connector member,
  the handle member connected to the first connector member connected to the intracardiac electrode,
  the first connector member comprising:
    a first insulating member,
    a plurality of first electrodes protruding from the first insulating member, and
    a first tubular member accommodating the first insulating member and the plurality of first electrodes;
  the second connector member comprising:
    a second insulating member having a plurality of longitudinal holes,
    a plurality of second electrodes disposed on an inner wall of the plurality of longitudinal holes, and
    a second tubular member accommodating the second insulating member;
  the first connector member and the second connector member being configured to be connectable to each other so that the plurality of first electrodes are insertable into the plurality of longitudinal holes of the second connector member, and the plurality of first electrodes are connectable to the plurality of second electrodes disposed in the plurality of longitudinal holes; and
  the first tubular member, the first insulating member, and the first electrodes configured, so that the first connector member comprises:
    a first space capable of containing at least a part of the second tubular member outside the first insulating member and inside the first tubular member when the first and second tubular members are connected,
    a second space not containing the first insulating member but containing the first electrodes,
    a third space containing neither the first insulating member nor the first electrodes; and
    the first space, the second space, and the third space being in this order from the side close to the handle member, wherein
  the second insulating member and the second tubular member are configured so that an entire circumferential edge of an end surface of the second insulating member, at which the plurality of longitudinal holes are formed, is directly contacted with and surrounded by an inner wall of the second tubular member.

2. The defibrillation system according to claim 1, wherein the longitudinal holes of the second insulating member have a part not having the second electrodes on an inner wall on the side close to the first insulating member when the second connector member is connected to the first connector member so that the first electrodes are inserted into the longitudinal holes of the second insulating member.

3. The defibrillation system according to claim 1, wherein when the first connector member is connected to the second connector member, the first insulating member of the first connector member and the second insulating member of the second connector member are in contact with each other.

4. The defibrillation system according to claim 1, wherein when the first connector member is connected to the second connector member, an end of the first tubular member of the first connector member is in contact with a part of the second connector member, and an end of the second tubular member of the second connector member is not in contact with any part of the first connector member.

5. The defibrillation system according to claim 1, wherein the second tubular member, the second insulating member, and the second electrodes are configured, so that the second connector member comprises a second space containing the second insulating member and the second electrodes on the side of the power supply part, and a third space contains neither the second insulating member nor the second electrodes.

6. The defibrillation system according to claim 5, wherein a length of the third space of the second tubular member in an axial direction is shorter than a length of the third space of the first tubular member in an axial direction.

7. The defibrillation system according to claim 1, wherein the intracardiac electrode comprises at least one intracardiac electrode A and at least one intracardiac electrode B;
the first connector member comprises a first connector member A connected to the intracardiac electrode A, and a first connector member B connected to the intracardiac electrode B; and
the second connector member comprises a second connector member A connected to the first connector member A and a second connector member B connected to the first connector member B.

8. The defibrillation system according to claim 7, wherein the first connector member A is connected to the second connector member A but is not connected to the second connector member B, and
the first connector member B is connected to the second connector B but is not connected to the second connector A.

9. The defibrillation system according to claim 1, wherein the second connector member is equipped with a disconnecting member for disconnecting the second connector member from the first connector member.

10. The defibrillation system according to claim 1, further comprising:
an electrocardiogram display that is connected to the power supply part and that transforms measured data by the defibrillation catheter into electrocardiogram, wherein
the plurality of second electrodes comprises at least one second electrode α that is connected to a power supply of the power supply part applying a pulse voltage to the defibrillation catheter and is connected to the electrocardiogram display, and at least one electrode β that is not connected to the power supply but is connected to the electrocardiogram display.

11. The defibrillation system according to claim 10, wherein a shortest distance between the second electrode α and the second electrode β is longer than a shortest distance between the second electrodes α.

12. A method of handling the defibrillation system according to claim 1, the method comprising:
inserting the second connector member into the first connector member by advancing the second connector member toward the side of the first connector member while keeping the first connector member stationary.

13. The defibrillation system according to claim 1, wherein
the plurality of first electrodes are accommodated by the first tubular member and not accommodated by the first insulating member,
the second tubular member, the second insulating member, and the second electrodes are configured, so that the second connector member comprises a second space containing the second insulating member and the second electrodes on the side of the power supply part, and a third space contains neither the second insulating member nor the second electrodes, and in the second space, an outer surface of the second insulating member is directly contacted with and surrounded by the inner wall of the second tubular member.

14. A defibrillation catheter comprising:

a catheter tube extending in a distal-proximal direction, at least one intracardiac electrode disposed on a distal side of the catheter tube, a handle member disposed on a proximal side of the catheter tube, and a first connector member having one end connected to the intracardiac electrode through the handle member and another end to be connected to a power supply part;

the first connector member comprising:

a first insulating member, a plurality of first electrodes protruding from the first insulating member, and a first tubular member accommodating the first insulating member and the plurality of first electrodes;

the first tubular member, the first insulating member, and the first electrodes configured, so that the first connector member comprises:

a fourth space being located outside the first insulating member and inside the first tubular member, a fifth space not containing the first insulating member but containing the first electrodes, a sixth space containing neither the first insulating member nor the first electrodes;

the fourth space, the fifth space, and the sixth space being in this order from the side close to the handle member, and the plurality of first electrodes are accommodated by the first tubular member and not accommodated by the first insulating member.

15. The defibrillation catheter according to claim 14, wherein the at least one intracardiac electrode comprises at least one intracardiac electrode A and at least one intracardiac electrode B;

the first connector member comprises a first connector member A connected to the intracardiac electrode A, and a first connector member B connected to the intracardiac electrode B; and one part of the plurality of first electrodes comprises at least one first electrode α connected to the intracardiac electrode A or the intracardiac electrode B, and another part of the plurality of first electrodes comprises at least one first electrode β connected to neither the intracardiac electrode A nor the intracardiac electrode B but connected to at least one intracardiac electrode C disposed on a distal side of the catheter tube.

* * * * *